(12) United States Patent
Levitsky et al.

(10) Patent No.: US 7,908,902 B2
(45) Date of Patent: Mar. 22, 2011

(54) AMPLIFIED SENSITIVITY OF POROUS CHEMOSENSORS BASED ON BERNOULLI EFFECT

(75) Inventors: Igor A. Levitsky, Fall River, MA (US); Young-Bin Park, White Plains, NY (US)

(73) Assignee: Emitech, Inc, Fall River, MA (US)

( * ) Notice: Subject to any disclaimer, the term of this patent is extended or adjusted under 35 U.S.C. 154(b) by 285 days.

(21) Appl. No.: 12/253,056

(22) Filed: Oct. 16, 2008

(65) Prior Publication Data

US 2010/0095743 A1 Apr. 22, 2010

(51) Int. Cl.
*G01N 7/00* (2006.01)
(52) U.S. Cl. ........................................ 73/31.07
(58) Field of Classification Search ................ 73/31.07, 73/863.81, 863.71
See application file for complete search history.

(56) References Cited

U.S. PATENT DOCUMENTS

| | | | |
|---|---|---|---|
| 4,856,328 A * | 8/1989 | Johnson | 73/202 |
| 6,455,184 B1 | 9/2002 | Peinecke | 429/514 |
| 6,668,663 B2 * | 12/2003 | May et al. | 73/861.05 |
| 7,305,895 B1 | 12/2007 | Andrews, Jr. et al. | 73/863.51 |
| 2006/0278253 A1 | 12/2006 | Verhaverbeke et al. | 134/1.3 |
| 2007/0160890 A1 | 7/2007 | Fischer | 429/414 |
| 2008/0025835 A1 | 1/2008 | Liljeroos | 414/804 |

* cited by examiner

*Primary Examiner* — Hezron Williams
*Assistant Examiner* — Tamiko D Bellamy

(57) ABSTRACT

A method of vapor sampling and its delivery to the porous sensory element(s) employed in chemical detectors/sensors for vapor(s) identification and quantification. The sampling and delivery system comprises a flow cell in which a sensory membrane is placed parallel to the flow, while an additional flow normal to the membrane is introduced using the Bernoulli effect. The bi-directional flow of vapors increases the interactions between the sensory material and vapor molecules, and enhances sensitivity.

14 Claims, 6 Drawing Sheets

AMPLIFIED SENSITIVITY OF POROUS CHEMOSENSORS BASED ON BERNOULLI EFFECT

STATEMENT OF GOVERNMENT INTEREST

The invention described herein may be manufactured and used by or for the Government of the United States of America for governmental purposes without the payment of any royalties thereon or therefore.

FIELD OF THE INVENTION

The present invention relates to a novel method for sampling and delivery of vapors for chemical sensing. This method discloses the application of a new flow cell design based on the Bernoulli principle to enhance the sensitivity of a sensor or sensor array that uses a sensory material entrapped in a porous membrane to detect analyte vapors.

BACKGROUND OF THE INVENTION

The invention generally relates to the sampling of vapors and their delivery to sensory elements in various chemical sensors or sensor arrays. Usually any sensor for detecting vapors, especially low pressure vapors, requires a sampling and delivery system. The most general sampling and delivery method is vapor pumping through a flow channel where the sensory element(s) is placed. The interaction of analyte vapors with the sensory element affects its physical-chemical properties (e.g., electrical conductivity, optical absorption, etc.), and their changes can be detected followed by analyte vapors identification and quantification.

To increase the sensitivity to analyte vapors, porous materials with a large surface area are employed. The porous medium can be sensitive itself or can be infiltrated with a sensory material. The major problem here is the vapor permeability through the pores, in which the topology can be branch-like (or pores can be partially clogged), making vapor diffusion inside the pores difficult. This factor can seriously detriment the sensor performance reducing its high sensitivity that is expected from the large surface area. If the average pore size of the sensory membrane is small (less than 1-2 μm), the pump cannot provide effective vapor delivery through the pores because of the low flow rate (flow normal to the membrane surface). Increasing the flow rate will require higher pump power and could result in the membrane breakdown.

Therefore, the sensory membrane should be fixed so that it will provide a flow parallel to its surface. In such a configuration, despite the absence of the flow rate limitation, vapors still cannot penetrate deep inside the membrane. Therefore, there is a need in the delivery method, which combines the parallel vapor flow with an effective permeability mechanism through the porous structure.

SUMMARY OF THE INVENTION

The present invention provides a novel method of vapor sampling and its delivery to the porous sensory element(s) employed in chemical detectors/sensors for vapor(s) identification and quantification. In this method, an additional channel for vapor delivery through the porous structure is employed, which is based on the Bernoulli effect. Thus, an amplified sensitivity is anticipated as compared to conventional methods where only one delivery channel is used.

In this invention, the sensory element (porous membrane) is placed in the flow channel in a special manner to provide the difference in the static pressure on both sides of the porous membrane due to the Bernoulli effect. It can be done by varying the width of two sub-channels or making the opening connecting the back side of the membrane to the ambient environment (subject of the vapor detection). The difference in vapor velocity on both sides of the membrane should result in the static pressure difference due to the Bernoulli effect. Consequently, the flow in the direction normal to the membrane surface should be generated, increasing the vapor interaction with the sensory material and thereby enhancing the detector sensitivity.

DESCRIPTION OF THE DRAWINGS

These and various other features and aspects of various exemplary embodiments will be readily understood with reference to the following detailed description taken in conjunction with the accompanying drawings, in which similar numbers are used throughout, and in which.

DETAILED DESCRIPTION OF THE INVENTION

Airflow must be frequently sampled for a variety of flow monitoring applications. Such sampling may be performed to examine the ambient air for chemical, biological and/or radiological particulates. Other purposes may include inertial characteristics of the airflows, such as pressure measurements. Finally, airflow sampling and delivery can be used in various chemical sensors, detectors, sensor arrays for identification and quantification of the specific target vapors (analytes) existing in the air (e.g. industrial toxic compounds, explosives, chemical/biological warfare agents). In this invention, the sampling/delivery system with improved characteristics will be considered as a part of the above chemical sensors. Thus, it can be incorporated in any chemical sensors to enhance/amplify the device sensitivity.

First, we will demonstrate that the porous sensory material has a significant advantage over the sensors based on flat solid films. Let us consider the fluorescence quenching of a solid sensory film as a transduction mechanism for the detection of analyte vapors. The same approach can be applied to any other transduction mechanism (e.g. conductivity, surface acoustic wave, plasmon resonance, etc.). The transduction mechanisms include an optical signal change (e.g., reflectance, absorption, luminescence), conductivity or resistivity change, resonance frequency of the acoustic signal change, etc.

Figure 1:
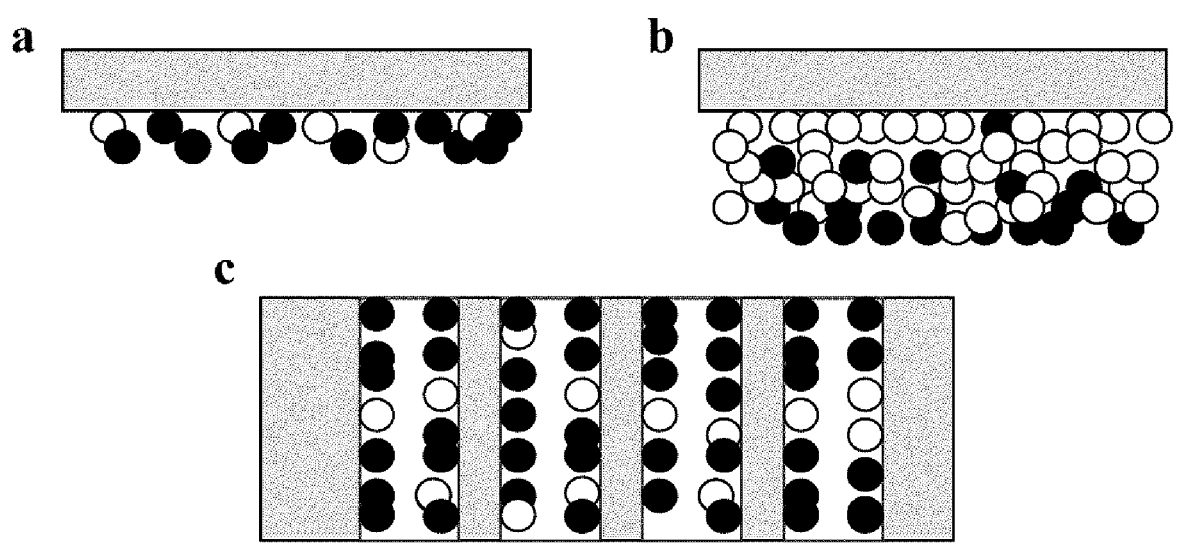
FIG. 1 Scheme demonstrating the different organization of sensory material: (a) high sensitivity and low responsive signal—thin film; (b) low sensitivity and high responsive signal—thick film; (c) high sensitivity and high responsive signal—nano/meso porous film. White and black circles denote unquenched and quenched sensory molecules/polymers, respectively.

The two main factors that govern the device sensitivity, $S=I_0/I$, are the initial amplitude of the signal ($I_0$) and the amplitude after an exposure to analyte vapor (I). The value of $I_0$ depends on the amount of deposited sensory molecules/polymers, and the value of I is defined by the analyte permeability. Here, we keep the other parameters constant, such as emissive yields, binding constants, film porosity, etc. A thin sensory film will provide a low $I_0$ value and high analyte permeability (FIG. 1a), so the maximum amount of molecules will be quenched. Experimentally, this means that despite high sensitivity, an initial signal can be comparable with the noise level, especially for a sensory monolayer. For a thick film, the $I_0$ amplitude can be high, but the vapor permeability is reduced at remote layers under the film surface (FIG. 1b). The use of the porous materials resolve this problem, since a sufficient amount of the sensory material is combined with high analyte permeability (FIG. 1c). However, most porous materials (e.g., sol-gel, zeolites, porous glasses, etc.) have random porosity and broad size distribution that lead to poor vapor permeability and interaction of the analyte molecules with sensory material inside the pores. This factor can seriously detriment the sensor performance reducing its high sensitivity expected from the large surface area of porous membrane. Therefore, a special method should be applied to efficiently deliver the vapors inside the nano/micro porous membrane.

Figure 2:
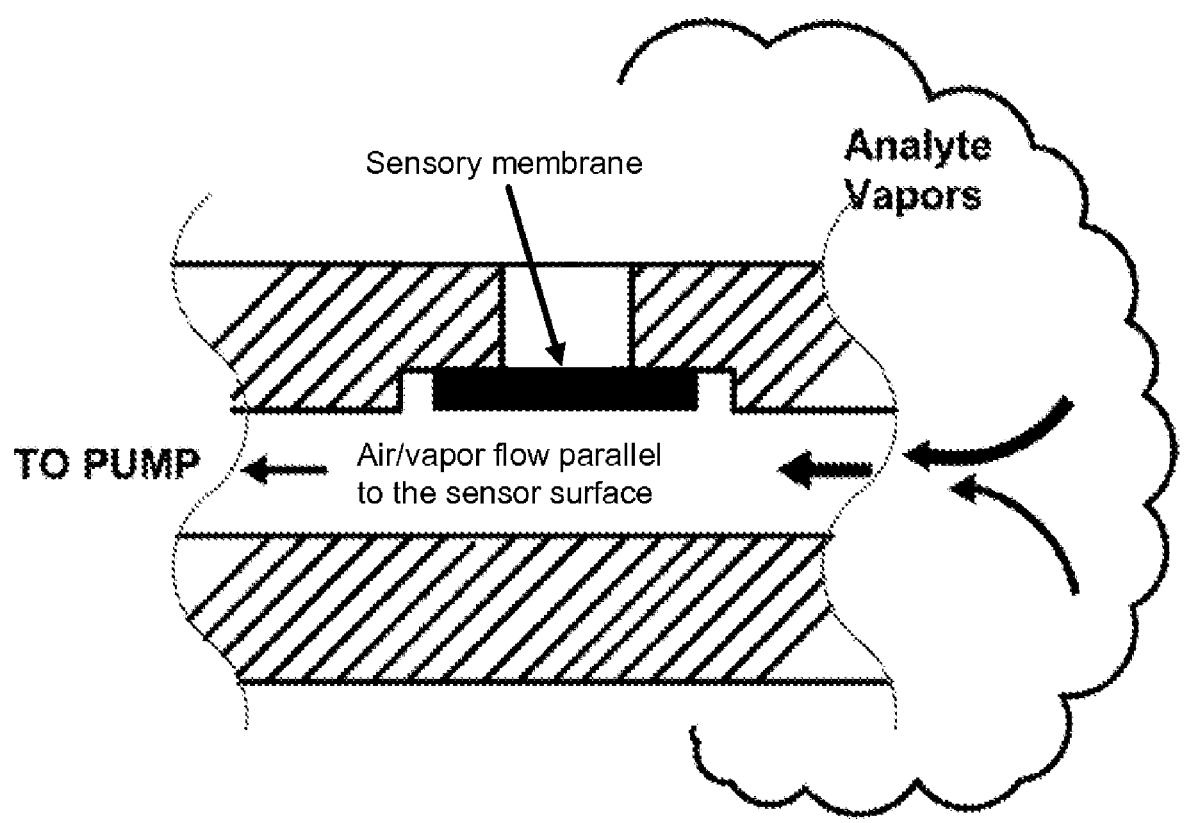
FIG. 2 Schematic of a non-porous sensory membrane placed in a flow cell such that the flow is parallel to the membrane surface.

At first sight, the direct airflow through the sensory membrane (normal to the membrane) could resolve this problem. However, the pump cannot provide effective vapor delivery through the pores since the pores of such small size (less than 1-2 µm) block airflow directed normal to the membrane surface. Increasing the flow rate will require higher pump power and could result in membrane breakdown. Therefore, to maintain a high flow rate, the sensory membrane usually is placed in a flow channel, so that the air flows in the direction parallel to the membrane surface (FIG. 2). The drawback of this design is the low vapor permeability through the pores.

Figure 3:
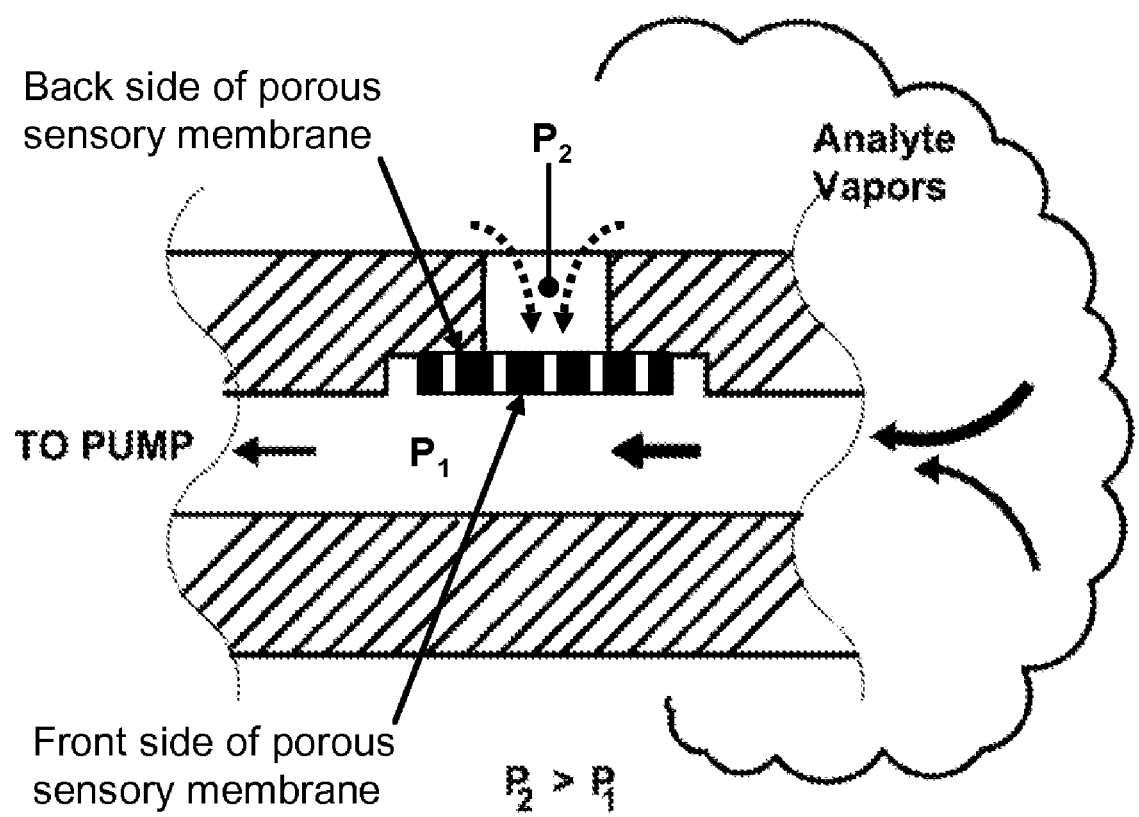
FIG. 3 Schematic of a porous sensor membrane placed in a flow cell such that a flow normal to the membrane surface through the wall opening (via pressure differences) results in enhanced sensitivity.

In this invention, we propose the use of the Bernoulli effect to improve vapor permeability through the porous sensory membrane. The Bernoulli principle is concerned with the relationship between static and dynamic pressures, such that $P=P_{stat}+P_{dyn}=\rho V^2/2$ is the dynamic pressure (where $\rho$ is the vapor density and V is the vapor velocity). Thus, the higher vapor velocity should result in lower static pressure. FIG. 3 shows the design of the flow cell where the back side of the sensory membrane is in contact with the ambient air through an opening and its front side is exposed to the parallel flow inside the flow cell. According to the Bernoulli effect, the static pressure at the back of the membrane, $P_2$ (FIG. 3), being higher than that at its front, $P_1$ (due to the moving flow), should initiate additional vapor flow through the porous membrane (dotted arrows, FIG. 3). Such additional flow normal to the membrane surface improves the vapor permeability through the sensory element(s) and consequently increases the device sensitivity.

To validate the Bernoulli effect, experiments has been conducted with aluminum oxide free standing membranes (100 nm pore size) filled with a fluorescent sensory polymer. Luminescent sensory material is selected from any group of sensory polymers and small molecules (e.g., conductive, emissive. non-emissive, acidic, basic); quantum dots, nanotubes or nanorods fabricated from II/VI, III/V or IV semiconductors (e.g. of CdS, CdSe, InP, GaAs, Ge, Si and doped Si), metal oxides (e.g., $TiO_2$ and $Al_2O_3$), Si oxide and carbon (e.g., carbon nanotubes or fullerenes).

Figure 4:
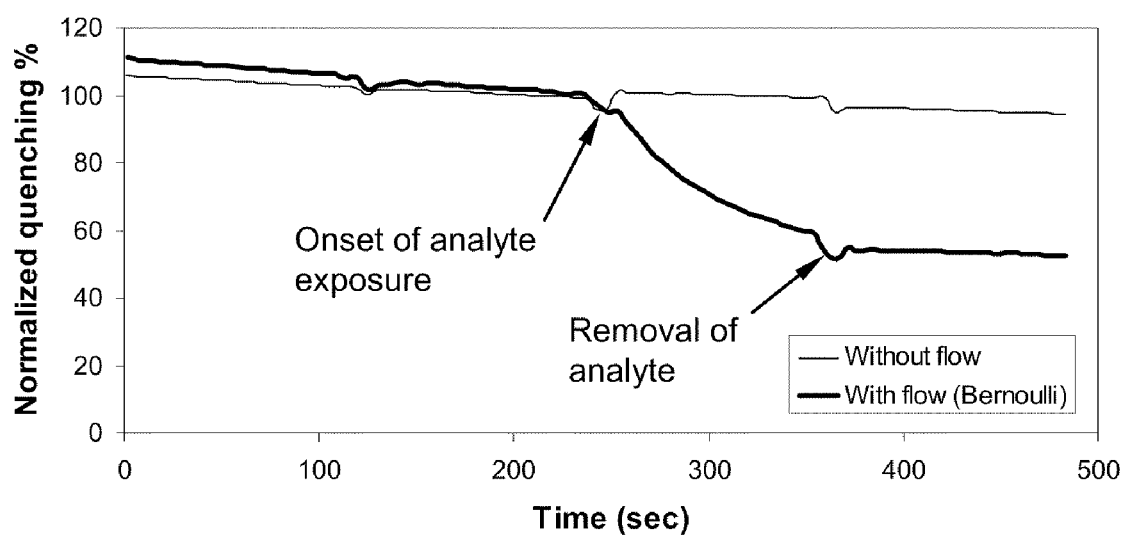
FIG. 4 Time traces demonstrating the effect of Bernoulli principle on the quenching behavior of a porous membrane infiltrated with a fluorescent polymer.

A sensory membrane was placed in the flow cell such that it covers the opening in the cell wall while exposing two sides—one side to the inner flow channel and the other to atmosphere (FIG. 3). The source of analyte vapor to which the fluorescent polymer is sensitive was brought from the outside in the proximity of the covered opening. (No analyte vapors were introduced into the cell through the cell entrance.) No fluorescence quenching was induced by the anlayte in the absence of the flow, i.e., when the pump was off. However, a sizable response was observed when the flow was introduced into the cell, i.e., when the pump was on such that the analyte vapors were drawn into the flow cell through the opening and consequently through the thickness of the membrane (FIG. 4). This proves that the Bernoulli effect can be employed to amplify the sensitivity by increasing the interaction between the sensory polymer and the anlayte molecules.

Figure 5:
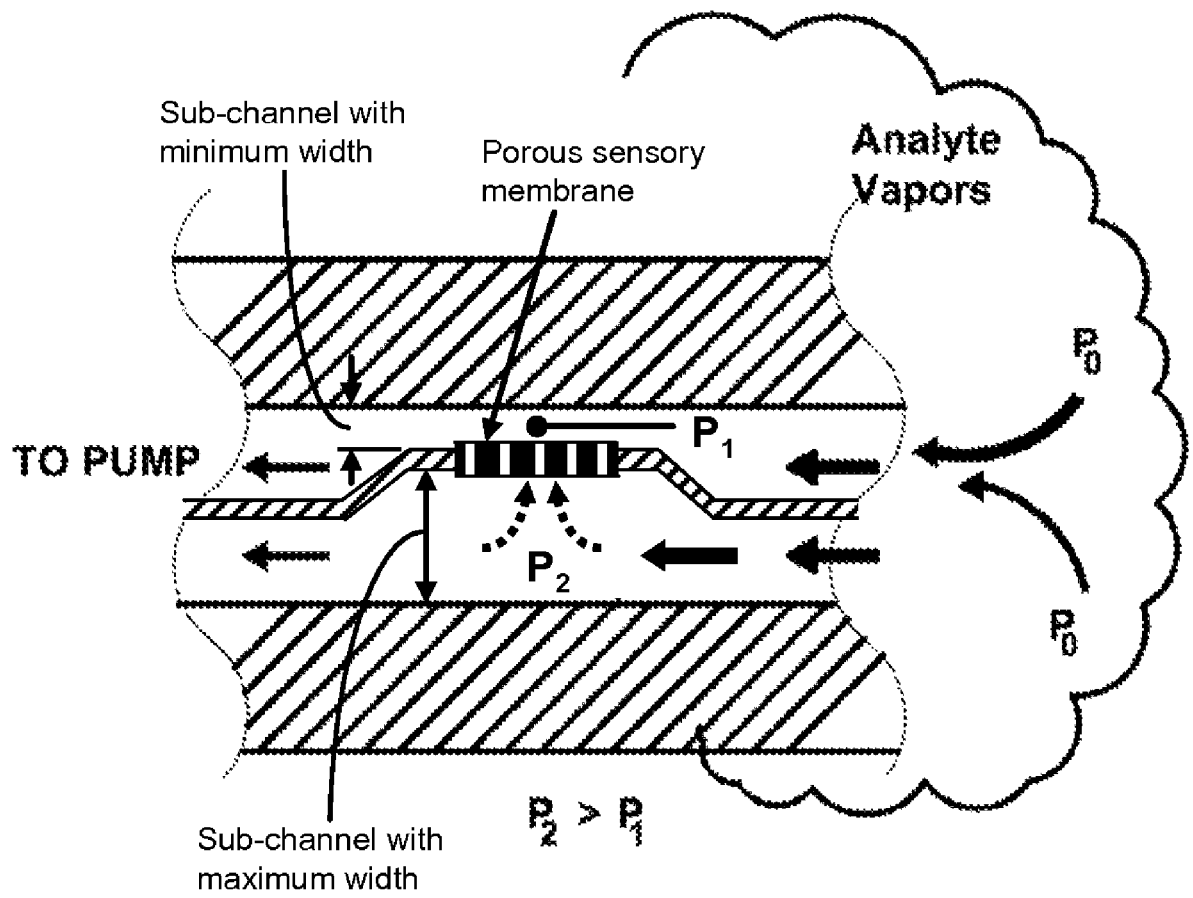
FIG. 5 Schematic of an asymmetrically partitioned flow cell with a suspended sensor membrane such that a flow normal to the membrane is generated according to the Bernoulli effect, resulting in enhanced sensitivity.

Another example (FIG. 5) shows the design of the flow cell divided into two sub-channels by a solid, concave wall with an opening connecting the two sub-channels in the place where they have maximum and minimum widths and a sensory membrane covering the opening. At the flow cell inlet, the static pressure, $P_0$, is equal in both of the sub-channels because of the same vapor/air velocity. However, different vapor velocities at both sides of the sensory membrane (as a result of different channel widths, FIG. 5) lead to different static pressures ($P_2>P_1$), which induces additional vapor flow through the pores (dotted arrows, FIG. 5). Such an additional flow normal to the membrane surface improves the vapor permeability through the sensory element(s) and consequently increases the device sensitivity. Another example (FIG. 6) demonstrates the concept design of the miniature optochemical sensor array (consisting of two sensory membranes) integrated with a wireless device, which uses the Bernoulli principle to amplify the system sensitivity. Its key part is the flow cell integrated with LED (2) and two photodiodes/filters (3a, 3b, 4a, 4b) in the wall of the flow channel. Two sensory elements (1a, 1b) are mounted on the opposite walls of the flow channel in front of the photodiodes. Each element represents the porous membrane (alumina or Si) infiltrated with two different sensory emissive polymers to provide chemical diversity for sensor selectivity. The porous membrane is selected from II/VI, III/V or IV semiconductors (e.g., of CdS, CdSe, InP, GaAs, Ge, Si and doped Si); zeolites; sol-gel, silicon oxide beads (synthethic opal); metal oxides (e.g., $TiO_2$ and $Al_2O_3$); porous glass, metal-organic frameworks (MOFs); polymers (e.g., electrospun polymer film, nylon membrane), carbon nanotubes (buckypaper).

Figure 6:
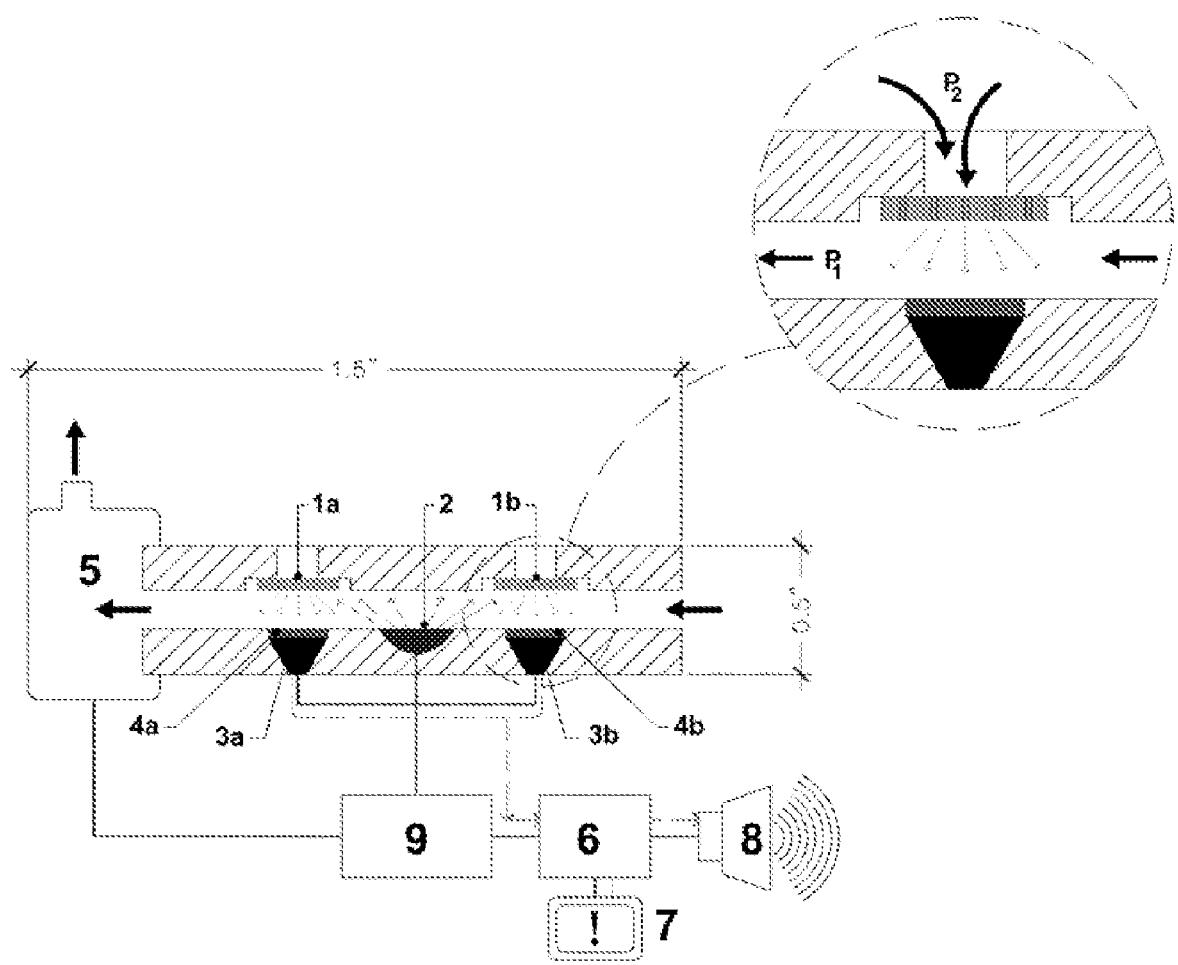
FIG. 6 Schematic of concept design of the miniature collection and sensor system for vapor detection: 1a, 1b—sensory elements; 2—LED; 3a, 3b—photodiodes; 4a, 4b—optical filters, 5—micropump; 6—microprocessor, 7—graphic visual interface, 8—wireless device; 9—rechargeable battery; brown lines—power supply links; pink lines—data exchange/communication. Inset shows how the Bernoulli effect will be used for sensitivity amplification.

Because of the porous structure, the lateral size can be small (~4×2 mm), and yet can provide a high photoluminescence signal output and enhanced sensitivity. For vapor sampling, a micropump (5) will be integrated in the flow cell exhaust. The microprocessor (6) reads the output signals from photodiodes through A/D interface, analyzes them according to the pattern recognition algorithm and in the case of target vapor detection, displays the alarm signal on the VGI (7). Then the personnel can trigger the wireless alarm manually (e.g. using a cell phone) or it can be done automatically (8). A rechargeable lithium-ion battery (9) provides the power supply for the functional modules of the sensor system. Inset to FIG. 6 shows how the Bernoulli effect amplifies the device sensitivity as a result of an additional flow directed normal to the porous sensory elements.

The following are claimed:

1. A vapor delivery and vapor sensory device with enhanced sensitivity comprised of a flat flow channel for vapor delivery in the direction parallel to the surface of a sensory element and an additional flow channel for vapor delivery in the direction both normal and through the entire surface of the sensory element as a result of the Bernoulli effect.

2. The sensory element according to claim 1, which is fixed in the wall of the flat flow channel so that its back side covers the opening connecting the flat flow channel and outer space through the opening in the wall.

3. The sensory element according to claim 1, wherein the sensory element is the porous membrane with a pore diameter in the range of 20-2000 nm.

4. The porous membrane as in claim 3, comprised solely of the porous structure which is specific to analyte vapor or porous membrane infiltrated with sensory material which is specific to analyte vapors.

5. A porous membrane as in claim 4, which is selected from II/VI, III/V or IV semiconductors; zeolites; sol-gel, silicon oxide beads; metal oxides; porous glass, metal-organic frameworks (MOFs); polymers, carbon nanotubes.

6. A sensory material as in claim 4, wherein said luminescent sensory material is selected from any group of sensory polymers and small molecules; quantum dots, nanotubes or nanorods fabricated from II/VI, III/V or IV semiconductors, metal oxides, Si oxide and carbon.

7. A vapor delivery and vapor sensory device as in claim 1, wherein the transduction mechanisms include an optical signal change, conductivity or resistivity signal change, resonance frequency of the acoustic signal change.

8. A vapor delivery and vapor sensory device with enhanced sensitivity comprised of a flat flow channel divided into two sub-channels by a solid, concave wall with a opening connecting two sub-channels in the place where they have maximum and minimum widths and sensory element fixed so that the opening is covered.

9. A vapor delivery and vapor sensory device according to claim 8, wherein the delivery of the vapors to the sensory elements occurs in the direction parallel to the surface of sensory element through two sub-channels and an additional flow channel in the direction normal to the surface of sensory element as a result of the Bernoulli effect.

10. The sensory element according to claim 8, wherein the sensory element is the porous membrane with a pore diameter in the range of 20-2000 nm.

11. The porous membrane as in claim 10, comprised solely of the porous structure which is specific to analyte vapor or porous membrane infiltrated with sensory material which is specific to analyte vapors.

12. A porous membrane as in claim 11, which is selected from II/VI, III/V or IV semiconductors; zeolites; sol-gel, silicon oxide beads; metal oxides; porous glass, metal-organic frameworks; polymers, carbon nanotubes.

13. A sensory material as in claim 11, wherein said luminescent sensory material is selected from any group of sensory polymers and small molecules; quantum dots, nanotubes or nanorods fabricated from II/VI, III/V or IV semiconductors, metal oxides, Si oxide and carbon.

14. A vapor delivery and vapor sensory device as in claim 8, wherein the transduction mechanisms include an optical signal change, conductivity or resistivity signal change, resonance frequency of the acoustic signal change.

* * * * *